United States Patent [19]

Pigneul et al.

[11] Patent Number: 4,790,838
[45] Date of Patent: Dec. 13, 1988

[54] DEVICE FORMING A SANITARY OR SIMILAR NAPKIN INCLUDING LATERAL WINGS OR FLAPS SEALED TOGETHER IMPROVING LATERAL TIGHTNESS, PREFERABLY PROVIDED WITH PLEATS

[75] Inventors: Raymond Pigneul, Durrenentzen; Rémy Ruppel, Horbourg, both of France

[73] Assignee: Beghin-Say SA, Thumeries, France

[21] Appl. No.: 97,154

[22] Filed: Sep. 16, 1987

[30] Foreign Application Priority Data

Oct. 6, 1986 [FR] France ................................. 86 13867

[51] Int. Cl.⁴ .............................................. A61F 13/16
[52] U.S. Cl. .................................. 604/366; 604/385.1
[58] Field of Search ..................... 604/385.1, 386, 366, 604/368, 387

[56] References Cited

U.S. PATENT DOCUMENTS

| | | | |
|---|---|---|---|
| 3,344,789 | 10/1967 | Arnold et al. | 604/368 |
| 3,523,536 | 8/1970 | Ruffo | 604/366 X |
| 4,059,114 | 11/1977 | Richards | 604/385.1 |
| 4,079,739 | 3/1978 | Whitehead | 604/385.1 |
| 4,324,246 | 4/1982 | Mullane et al. | 604/366 |
| 4,701,177 | 10/1987 | Ellis et al. | 604/385.2 |

Primary Examiner—John D. Yasko
Attorney, Agent, or Firm—A. W. Breiner

[57] ABSTRACT

This invention involves a device forming a sanitary napkin.

The device includes a preformed, usually biconcave fluid-absorbent pad component (2) defining a biconcave central area (8) of reduced width, entirely arranged inside a covering (10) which is permeable to said fluids, and a layer (16) made of a component impermeable to fluids which is inserted between the pad component (2) and said covering (10), characterized in that said covering (10) is designed with a width (L) larger than width (l) of said pad component (2) at the level of said biconcave reduced-width area (8), thus defining side wings or flaps (20, 22) that are sealed together.

This device improves lateral tightness while providing excellent comfort.

10 Claims, 1 Drawing Sheet

DEVICE FORMING A SANITARY OR SIMILAR NAPKIN INCLUDING LATERAL WINGS OR FLAPS SEALED TOGETHER IMPROVING LATERAL TIGHTNESS, PREFERABLY PROVIDED WITH PLEATS

This invention involves primarily a device forming a sanitary or similar napkin including lateral wings or flaps sealed together, which improve lateral tightness and are preferably provided with pleats.

Many devices forming sanitary or similar napkins, particularly for woman's hygiene, are already known.

For example, U.S. Pat. No. 3,805,790 describes a device forming a sanitary napkin including a preformed, usually biconcave fluid-absorbent pad component (16) defining an intermediate bioconcave area of reduced width.

Such pad component (16) is entirely arranged inside a covering defined by an upper film (20) that is permeable to fluids and a lower film (18) that is impermeable to fluids.

The dimensions of the covering are adjusted to the shape of the absorbent pad component so as to hem it in tightly without any play; so, the covering is of same biconcave shape.

It is emphasized that the biconcave shape improves the patient's comfort (see column 5, lines 42-49).

Also, U.S. Pat. No. 2,331,355 discloses a device forming a similar sanitary napkin, additionally including one or more central pleats allowing to define a curved, fluid-receiving area. The pleats are arranged in the lengthwise central area of the device (see FIGS. 1–28).

U.S. Pat. No. 3,203,419 further describes a device forming a sanitary napkin, and a manufacturing process for said napkin.

According to that device, the absorbent pad component (10) is entirely arranged inside a covering which is permeable to fluids and closed at the junction of a lower film (11) and an upper film (11), which are then sealed together (see FIG. 3). Layer (16) of the component impermeable to fluids is inserted between pad component (10) and covering (11).

According to that device, the pad component shows a biconvex shape in lengthwise axial section, and straight side edges (see FIG. 2), which is unfavorable in terms of comfort and fails to provide proper lateral tightness.

European Application No. 67,377 further describes a device forming a sanitary napkin including a biconcave pad component whose concavity is achieved through precompression of the pad component with a view to improved comfort.

The degree of compression is such that pad component width is reduced by at least 10% at compression level.

Here again, the size of covering (2) is strictly the same as the compressed pad component (see FIG. 2).

U.S. Pat. No. 3,575,174 further discloses a similar device according to which the sanitary napkin is curved from the front end to the rear end so as to give it the shape of a saucer. Lengthwise grooves (20) and two crosswise grooves (22) are provided near the front end and near the rear end (see FIGS. 4 and 5).

European Application No. 136,524 discloses a device forming a sanitary napkin provided with grooves curving the device in such a manner that it produces and improves the body conformation of the person wearing the device.

Lastly, European Pat. No. 137,725 discloses a device forming a sanitary napkin including a two-dimensional, elongated absorbent pad component surrounded by a peripheral edge of higher density so as to provide improved tightness.

All known devices, particularly those mentioned above, are not fully satisfactory yet in terms of lateral tightness, although some of them have provided satisfactory solutions in terms of comfort.

The main purpose of this invention is to provide a device forming a sanitary or similar napkin ensuring increased lateral tightness with a view to preventing any lateral leakage of fluids.

Thus, this invention provides a device forming a sanitary or similar napkins, in particular for woman's hygiene, including a preformed, usually biconcave fluid-absorbent pad component defining a biconcave area of reduced width, entirely arranged inside a covering that is permeable to said fluids, and a layer of a component that is impermeable to fluids and is inserted between the pad component and said covering, characterized in that said covering is designed with a larger width than that of said pad component at the level of said biconcave, reduced-width area, thus defining lateral wings or flaps that are sealed together so as to improve lateral tightness to said fluids.

According to a preferred characteristic of the invention, the lateral wings or flaps are provided with one or more pleats that are sealed together and further improve lateral tightness.

According to a special production method, sealing of both the lateral wings or flaps and the above mentioned pleats is made using an adhesive glue, preferably of the hot-melt type, that is, a glue becoming fluid when heated.

According to a particular advantageous feature, the above mentioned pleats are shaped as arcs of a circle that are concentric with the adjacent concavity.

According to a further advantageous feature, the device of the invention includes one or more grooves shaped in the mass of the pad component in the central area defined between the above mentioned lateral concavities.

Advantageously, the grooves are also shaped as arcs of a circle preferably concentric with the above mentioned concavities.

According to a further particular feature, the above mentioned pleats and grooves are arranged symmetrically with reference to the lengthwise plane of symmetry of the sanitary napkin.

The above mentioned grooves can be produced by any appropriate means. However, the grooves are preferably produced by compression of the absorbent pad, using any appropriate compression tool such as a pressure roller.

Further aims, features and advantages will clearly appear in the light of the following explanatory description referring to the drawings appended hereto, showing a currently preferred method of production of the invention which is shown merely for illustrative purposes and, therefore, does in no way restrict the scope of this invention.

Figure 1:
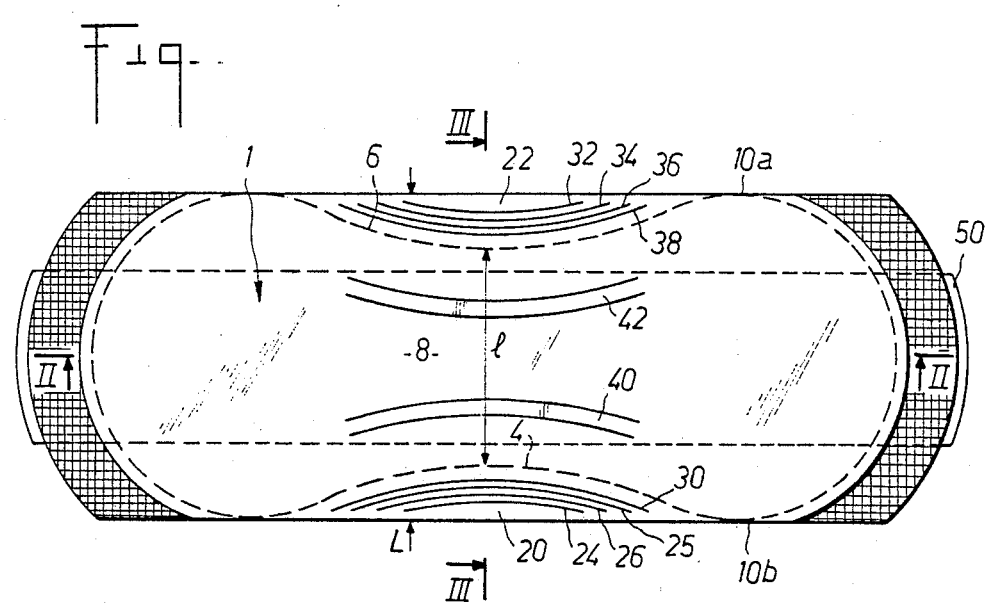
FIG. 1 is a top view of the current preferred device forming a sanitary napkin according to the invention.
Figure 2:
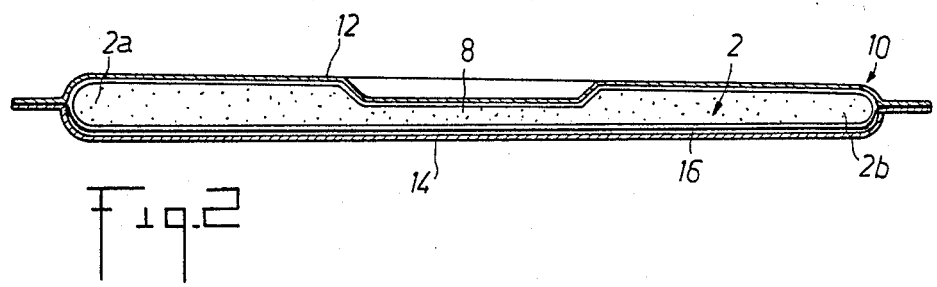
FIG. 2 is a lengthwise sectional view along line II—II, passing through a groove of the central area.
Figure 3:
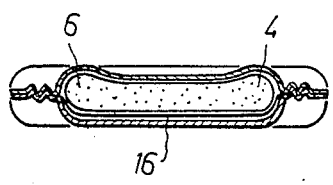
FIG. 3 is a crosswise sectional view along line III—III of FIG. 1.

With reference to FIGS. 1-3, a device forming a sanitary or similar napkin according to the invention, represented by general reference number 1, includes a preformed, fluid-absorbent pad component (2) that is usually biconcave due to the presence of concave lateral edges (4, 6), defining a biconcave central area (8) of reduced width with respect to front end area (2a) and rear end area (2b).

Such pad component (2) is arranged, according to the example shown, entirely inside a covering (10) that is permeable to said fluids and may be defined for example by the linking of an upper film (12) which is permeable to fluids and a lower film (14) which may be permeable to fluids, too.

When the lower film (14) is permeable to fluids, it is produced similarly to film (12) and may come from a single strip shaped as a covering to receive the pad component (2) inside.

Thus, a simplification of the manufacturing process is achieved.

Such proceses are well known and are described for example in the above mentioned U.S. Pat. Nos. 3,203,419 and 3,575,174.

This device also includes usually a layer (16) of a component that is impermeable to fluids and inserted between the pad component (2) and covering (10), usually between pad component (2) and lower film (14) opposite to upper film (12) designed to receive the above mentioned fluids.

According to this invention, covering (10) is designed with a width (L) larger than width (l) of pad component (2) at the level of biconcave area (8), thus defining lateral wings or flaps (20, 22) which are sealed together. Outside the biconcave area, the covering is adjusted to the shape of pad component (2), so as to hem it in tightly without any play.

Thus, the device's lateral tightness to fluids is radically improved, which prevents any accidental leakage of fluids.

It should be noted that said lateral wings or flaps (20, 22) are produced in a simple way of designing a covering (10) with straight edges (10a, 10b), as is clearly visible in FIG. 1.

Preferably, lateral wings or flaps (20, 22) include one or more pleats, respectively (24, 26, 28, 30) for wing or flap (20) and (32, 34, 36, 38) for wing or flap (22).

Such pleats (24-38) are sealed together, which further improves lateral tightness. Sealing of the lateral wings or flaps is preferably achieved using an adhesive glue, advantageously of the hot-melt type so that they are produced automatically when upper film (12) and lower film (14) are being sealed together.

The pleats can be easily produced, using engraved shaping rollers, that is, rollers with appropriately shaped grooves, such roller types being well known to specialists.

Based on a particularly advantageous feature of the invention, pleats (20-38) are shaped in the form of arcs of a circle concentric with the adjacent concavity.

Thus, pleats (24, 26, 28, 30) are concentric with adjacent concavity (4), whereas pleats (32, 34, 36, 38) are concentric with adjacent concavity (6).

So, it can be understood that, due to the device's biconcavity, the pleats are produced symmetrically with respect to the longitudinal plane of symmetry of the device.

According to a further characteristic of the device based on the invention, the device has one or more grooves (40, 42) provided in the mass of the pad component (2) in the central area (8) defined between lateral concavities (4, 6).

Advantageously, said grooves (40, 42) are themselves shaped as arcs of a circle, preferably concentric with adjacent concavities (4) and (6) respectively, so that the component is arranged symmetrically with respect to the longitudinal plane of symmetry of the device.

Said grooves (40, 42) are advantageously produced by compression of absorbent pad (2), using any appropriate compressive means such as a pressure roller with a shoulder of matching shape as a specialist can clearly understand.

The presence of grooves (40, 42) is advantageous in combination with the lateral wings or flaps, in that it gives the device forming a sanitary napkin a tendency to get deformed in a saucer-type shape as the wearer moves, facilitating reception of the above mentioned fluids and fluid flowing towards the central section of the device.

So, it is understandable that the invention provides a device forming a sanitary napkin that guarantees almost total lateral tightness while providing a high degree of comfort.

Naturally, the invention includes any systems forming technical equivalents of the systems described herein and the various combinations thereof.

So, it can be easily understood that the dimensions of the basic component of the device may vary; similarly, the materials used for the various components may be either of a conventional nature or of a special nature to meet a specific use. Generally, the components are made of conventional materials: for example, the pad component (2) is made of cellulose foam in which hydrophilic polymers with a high absorbing power may be incorporated.

Layer (16), which forms the component impermeable to fluids, may be made of a plastic material such as polythene or similar.

Also, the covering may be made of a woven or nonwoven gauze permeable to fluids, which may be hydrophobic, as is well known.

Similarly, the outside of lower film (14) may be provided with an adhesive layer, advantageously of the hot-melt type, covered with a protective strip (50) that can be removed for the purpose of easier sticking to an undergarment, as is well known, too.

Lastly, layer (16) impermeable to fluids may be sealed or glued to lower film (14) of the covering, or even form an integral part of the latter and thus form said lower film (14).

We claim:

1. Article for forming a sanitary or similar napkin, in particular for women's hygiene, including a preformed fluid-absorbent pad component defining a central biconcave area of reduced width, entirely arranged inside a covering that is permeable to said fluids, and a layer of a component impermeable to fluids which is inserted between said pad component and said covering, characterized in that said covering is designed with a width larger than the width of said pad component at the point of said reduced-width biconcave area, thus defining lateral wings or flaps that are sealed together so as to improve lateral tightness to said fluids, said lateral wings or flaps being provided with one or more pleats shaped as arcs of a circle which are concentric with adjacent concavity that are sealed together, further improving lateral tightness.

2. The article of claim 1 wherein said lateral wings or flaps and pleats are made using an adhesive glue.

3. The article of claim 2 wherein said adhesive glue is of the hot-melt type.

4. The article of claim 1 including one or more grooves shaped in the mass of said pad component in the central area defined between said concavities.

5. The article of claim 4 wherein said grooves are shaped as arcs of a circle.

6. The article of claim 5 wherein said grooves are concentric with said concavities.

7. The article of claim 5 wherein said grooves are shaped by compression of the absorbent pad through any appropriate compressive system, such as a pressure roller.

8. The article of claim 1 wherein said covering has straight lateral edges which define said wings or flaps at the point of said concavities of said pad.

9. The article of claim 1 wherein said covering is defined by an upper film and a lower film, and said layer which is impermeable to fluids is sealed or glued to the lower film.

10. The article of claim 9 wherein said layer is integral with said lower film.

* * * * *